US008829174B2

(12) United States Patent
Weiner et al.

(10) Patent No.: US 8,829,174 B2
(45) Date of Patent: Sep. 9, 2014

(54) HCV VACCINES AND METHODS FOR USING THE SAME

(75) Inventors: David B Weiner, Merion, PA (US); Krystle A. Lang Kuhs, Bethesda, MD (US); Jian Yan, Havertown, PA (US); Ruxandra Draghia-Akli, Brussels (BE); Amir Khan, The Woodlands, TX (US)

(73) Assignees: The Trustees of the University of Pennsylvania, Philadelphia, PA (US); Inovio Pharmaceuticals, Inc., Blue Bell, PA (US)

( * ) Notice: Subject to any disclaimer, the term of this patent is extended or adjusted under 35 U.S.C. 154(b) by 377 days.

(21) Appl. No.: 13/127,008

(22) PCT Filed: Oct. 29, 2008

(86) PCT No.: PCT/US2008/081627

§ 371 (c)(1),
(2), (4) Date: Jul. 20, 2011

(87) PCT Pub. No.: WO2010/050939

PCT Pub. Date: May 6, 2010

(65) Prior Publication Data

US 2012/0034256 A1 Feb. 9, 2012

(51) Int. Cl.

| | |
|---|---|
| ***C12N 15/57*** | (2006.01) |
| ***C12N 15/51*** | (2006.01) |
| ***C12N 15/74*** | (2006.01) |
| ***C12N 15/79*** | (2006.01) |
| ***C12N 9/50*** | (2006.01) |

(52) U.S. Cl.
USPC ...... 536/23.2; 435/69.1; 435/91.21; 435/219; 435/252.3; 435/320.1; 536/23.1; 536/23.72

(58) Field of Classification Search
None
See application file for complete search history.

(56) References Cited

U.S. PATENT DOCUMENTS

| | | | |
|---|---|---|---|
| 4,510,245 | A | 4/1985 | Cousens et al. |
| 4,722,848 | A | 2/1988 | Paoletti et al. |
| 4,790,987 | A | 12/1988 | Compans et al. |
| 4,797,368 | A | 1/1989 | Carter et al. |
| 4,920,209 | A | 4/1990 | Davis et al. |
| 4,945,050 | A | 7/1990 | Sanford et al. |
| 5,017,487 | A | 5/1991 | Stunnenberg et al. |
| 5,036,006 | A | 7/1991 | Sanford et al. |
| 5,077,044 | A | 12/1991 | Stocker et al. |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicali et al. |
| 5,294,441 | A | 3/1994 | Curtiss, III |
| 5,294,548 | A | 3/1994 | McLinden et al. |
| 5,310,668 | A | 5/1994 | Ellis et al. |
| 5,387,744 | A | 2/1995 | Curtiss, III et al. |
| 5,389,368 | A | 2/1995 | Cursiss, III |
| 5,424,065 | A | 6/1995 | Curtiss, III et al. |
| 5,451,499 | A | 9/1995 | Cochran |
| 5,453,364 | A | 9/1995 | Paoletti |
| 5,462,734 | A | 10/1995 | Letchworth, III et al. |
| 5,470,734 | A | 11/1995 | Sondermeijer et al. |
| 5,474,935 | A | 12/1995 | Chatterjee et al. |
| 5,482,713 | A | 1/1996 | Paoletti |
| 5,580,859 | A | 12/1996 | Felgner et al. |
| 5,591,439 | A | 1/1997 | Plotkin et al. |
| 5,593,972 | A | 1/1997 | Weiner et al. |
| 5,643,579 | A | 7/1997 | Hung et al. |
| 5,650,309 | A | 7/1997 | Wong-Staal et al. |
| 5,676,594 | A | 10/1997 | Joosten |
| 5,698,202 | A | 12/1997 | Ertl et al. |
| 5,703,055 | A | 12/1997 | Felgner et al. |
| 5,739,118 | A | 4/1998 | Carrano et al. |
| 5,817,637 | A | 10/1998 | Weiner et al. |
| 5,830,876 | A | 11/1998 | Weiner et al. |
| 5,955,088 | A | 9/1999 | Ghiasi et al. |
| 5,962,428 | A | 10/1999 | Carrano et al. |
| 5,981,505 | A | 11/1999 | Weiner et al. |
| 6,034,298 | A | 3/2000 | Lam et al. |
| 6,042,836 | A | 3/2000 | Berman et al. |
| 6,127,116 | A | 10/2000 | Rice et al. |
| 6,156,319 | A | 12/2000 | Cohen et al. |
| 6,589,529 | B1 | 7/2003 | Choi et al. |
| 7,245,963 | B2 | 7/2007 | Draghia-Akli et al. |
| 2004/0247615 | A1 | 12/2004 | Emini et al. |
| 2005/0052630 | A1 | 3/2005 | Smith et al. |
| 2006/0093617 | A1 | 5/2006 | Buyse et al. |
| 2008/0091135 | A1 | 4/2008 | Draghia-Akli et al. |

FOREIGN PATENT DOCUMENTS

| | | |
|---|---|---|
| WO | 94/16737 | 8/1994 |
| WO | WO2006133911 | 12/2006 |
| WO | WO2007031867 | 3/2007 |

OTHER PUBLICATIONS

Weiner, A.J. et al., "Intrahepatic genetic inoculation of hepatitis C virus RNA confers cross-protective immunity", J. Virol, 2001, 75:7142-5148.

Bassett S.E. et al., "Protective immune response to hepatitis C virus in champanzees rechallenged following clearance of primary infection", Hepatology, 2001, 33:1479-1487.

(Continued)

*Primary Examiner* — Michelle S Horning

(74) *Attorney, Agent, or Firm* — Pepper Hamilton LLP

(57) ABSTRACT

Improved anti-HCV immunogens and nucleic acid molecules that encode them are disclosed. Immunogens disclosed include those having consensus HCV genotype 1 a/1 b NS3 and NS4A. Pharmaceutical composition, recombinant vaccines comprising and live attenuated vaccines are disclosed as well methods of inducing an immune response in an individual against HCV are disclosed.

25 Claims, 6 Drawing Sheets

(56) References Cited

OTHER PUBLICATIONS

Lanford, R.E. et al., "Cross-genotype immunity to hepatitis C virus", J. Virol, 2004, 78:1575-1581.
Houghton, M. et al., "Prospects for a vaccine against the hepatitus C virus", Nature, 2005, 436:961-966.
Frelin, L. et al., "Low dose and gene gun immunization with a hepatitis C virus nonstructural (NS) 3 DNA-based vaccine containing NS4A inhibit NS3/4A-expresssing tumors in vivo", Gene Therapy, 2003, 10:686-699.
Wolk, B. et al. "Subcelluar localization, stability, and trans-cleavage competence of the hepatitis C virus NS3-NS4A complex expressed in tetracycline-regulated cell lines", J. Virol., 2000, 74:2293-2304.
Tanji, Y et al., "Hepatitis C virus-encoded nonstructural protein NS4A has versatile functions in viral protein processing", J. Virol., 1995, 69:1575-1581.
Cooper, S. et al., "Analysis of a successful immune response against hepatitis C virus", Immunity, 1999, 10:439-449.
Post, J.J. et al., "Clearance of hepatitis C viremia associated with cellular immunity in the absence of seroconversion in the hepatitis C incidence and transmission in prisons study cohort", J. Infect. Dis., 2004, 189:1846-1855.
Lechner, F. et al., "Analysis of successful immune responses in persons infected with hepatitis C virus", J Exp Med, 2000, 191:1499-1512.
Rehermann, B. et al., "Quantative analysis of the peripheral blood cytotoxic T lymphocyte response in patients wth chronic hepatitis C virus infection", J Clin Invest, 1996, 98:1432-1440.
Thimme, R. et al., "Determinants of viral clearance and persistence during acute hepatitis C virus infection", J Exp Med, 2001, 194:1395-1406.
Nelson, D.R. et al., "The role of hepatitus C virus-specific cytotoxic T lymphocytes in chronic hepatitis C", J Immunol, 1997, 158:1473-1481.
Missale, G. et al., "Differenct clinical behaviors of acute hepatitis C virus infection are associated with different vigor of the anti-viral cell-mediated immune response", J Clin Invest, 1996, 98:706-714.
Diepolder, H.M. et al., "Possible mechanism involving T-lymphocyte response to non-structural protein 3 in viral clearance in acute hepatitis C virus infection", Lancet, 1995, 346:1006-1007.
Chattergoon, M. et al., "Genetic immunization: a new era in vaccines and immune therapeutics", FASEB J, 1997, 11:753-763.
Liu, M.A. et al., "Human clinical trials of plasmid DNA vaccines", Adv Genet, 2005, 55:25-40.
Capone, S et al., "Modulation of the immune response induced by gene elecrotransfer of a hepatitis C DNA vaccine in nonhuman primates", J Immunol, 2006, 177:7462-7471.
Yan, J. et al., "Enhanced cellular immune responses elicited by an engineered HIV-1 subtype B consensus-based envelope DNA vaccine", Mol Ther, 2007, 15:411-421.
Ahlen, G. et al., "In vivo electroporation enhances the immunogenicity of hepatitis C virus nonstructural 3/4A DNA by increased local DNA uptake, protein expression, inflammation, and infiltration of CD3+T cells", J Immunol, 2007, 179:4741-4753.
Frelin, L. et al., "Codon optimization and mRNA amplification effectively enhances the immunogenicity of the hepatitis C virus nonstructural 3/4A gene", Gene Therapy, 2004, 11:522-533.
Lang, K.A. et al., "Strong HCV NS3- and NS4A-specific cellular immune responses induced in mice and *Rhesus macaques* by a novel HCV genotype 1a/1b consensus DNA vaccine", Vaccine, 2008, 26:6225-6231.
GenBank Accession No. DQ485330, Apr. 29, 2007.

HCV VACCINES AND METHODS FOR USING THE SAME

CROSS-REFERENCE TO RELATED APPLICATIONS

This application is the U.S. National Stage filing of International Application Serial No. PCT/US2008/081627, filed Oct. 28, 2008, which is incorporated herein by reference in its entirety.

FIELD OF THE INVENTION

The present invention relates to improved HCV, improved methods for inducing immune responses, and for prophylactically and/or therapeutically immunizing individuals against HCV.

BACKGROUND OF THE INVENTION

Hepatitis C (HCV) is a small enveloped, positive stranded RNA virus that represents a major health burden worldwide with more than 170 million individuals currently infected [Thomson, B. J. and R. G. Finch, Hepatitis C virus infection. Clin Microbiol Infect, 2005. 11(2): p. 86-94]. One of the most successful of all human viruses, HCV preferentially infects heptocytes and is able to persist in the livers of up to 70% of all infected individuals [Bowen, D. O. and C. M. Walker, Adaptive immune responses in acute and chronic hepatitis C virus infection. Nature, 2005. 436(7053): p. 946-52]. It is estimated that up to 30% of chronically infected individuals will develop progressive liver disease, including cirrhosis and hepatocellular carcinoma (HCC) during their lifetime making HCV infection the leading causes of liver transplantation in the world. In addition, HCV and HBV infections are implicated in 70% of all cases of HCC, which is the third leading cause of cancer deaths worldwide [Levrero, M., Viral hepatitis and liver cancer: the case of hepatitis C. Oncogene, 2006. 25(27): p. 3834-47].

Due to the persistent nature of the virus, HCV infection can be extremely difficult and expensive to treat. Most infected individuals do not receive treatment. However, those that do, pay on average 17,700 to 22,000 dollars for standard treatment protocols [Salomon, J. A., et al., Cost-effectiveness of treatment for chronic hepatitis C infection in an evolving patient population. Jama, 2003. 290(2): p. 228-37]. Genotype 1 infection, the most prevalent in Europe and North America, has the poorest prognosis with as little as 42% of individuals responding to standard treatments [Manns, M. P., et al., Peginterferon alfa-2b plus ribavirin compared with interferon alfa-2b plus ribavirin for initial treatment of chronic hepatitis C: a randomised trial. Lancet, 2001. 358(9286): p. 958-65].

Therefore, the high prevalence of infection, lack of effective treatments and economic burden of chronic HCV, illustrates the urgent need for the development of novel immune therapy strategies to combat this disease. Currently there is no prophylactic or therapeutic vaccine for HCV, however there is evidence that natural and protective immunity to HCV exists [Weiner, A. J., et al., Intrahepatic genetic inoculation of hepatitis C virus RNA confers cross-protective immunity. J Virol, 2001. 75(15): p. 7142-8; Bassett, S. E., et al., Protective immune response to hepatitis C virus in chimpanzees rechallenged following clearance of primary infection. Hepatology, 2001. 33(6): p. 1479-87; Lanford, R. E., et al., Cross-genotype immunity to hepatitis C virus. J Virol, 2004. 78(3): p. 1575-81]. In the majority of cases, convalescent humans are not protected against acute HCV infection, but rather, they are protected from the progression of infection to a chronic state [Houghton, M. and S. Abrignani, Prospects for a vaccine against the hepatitis C virus. Nature, 2005. 436(7053): p. 961-6]. Since it is the chronic state of infection that is mainly associated with HCV pathogenicity, this argues for the feasibility of a vaccine approach to control or treat this infection.

Understanding the adaptive immunity to this virus is critical for designing strategies, such as DNA vaccines, to combat viral infection. Although virus-specific antibodies are detected within 7-8 weeks post HCV infection [Pawlotsky, J. M., Diagnostic tests for hepatitis C. J Hepatol, 1999. 31 Suppl 1: p. 71-9] they do not protect against reinfection [Farci, P., et al., Lack of protective immunity against reinfection with hepatitis C virus. Science, 1992. 258(5079): p. 135-40; Lai, M. E., et al., Hepatitis C virus in multiple episodes of acute hepatitis in polytransfused thalassaemic children. Lancet, 1994. 343(8894): p. 388-90] and can be completely absent following the resolution of infection [Cooper, S., et al., Analysis of a successful immune response against hepatitis C virus. Immunity, 1999. 10(4): p. 439-49; Post, J. J., et al., Clearance of hepatitis C viremia associated with cellular immunity in the absence of seroconversion in the hepatitis C incidence and transmission in prisons study cohort. J Infect Dis, 2004. 189(10): p. 1846-55]. Instead, infected individuals that mount an early, multi-specific, intrahepatic CD4+ helper and CD8+ cytotoxic T-cell response can eliminate HCV infection [Lechner, F., et al., Analysis of successful immune responses in persons infected with hepatitis C virus. J Exp Med, 2000. 191(9): p. 1499-512; Gerlach, J. T., et al., Recurrence of hepatitis C virus after loss of virus-specific CD4(+) T-cell response in acute hepatitis C. Gastroenterology, 1999. 117(4): p. 933-41; Thimme, R., et al., Determinants of viral clearance and persistence during acute hepatitis C virus infection. J Exp Med, 2001. 194(10): p. 1395-406; Grakoui, A., et al., HCV persistence and immune evasion in the absence of memory T cell help. Science, 2003. 302(5645): p. 659-62]. In fact, it has been shown that an important correlate to resolution of acute infection is a strong T cell response against the structural proteins of the virus, in particular the NS3 protein [Missale, G., et al., Different clinical behaviors of acute hepatitis C virus infection are associated with different vigor of the anti-viral cell-mediated immune response. J Clin Invest, 1996. 98(3): p. 706-14; Diepolder, H. M., et al., Possible mechanism involving T-lymphocyte response to non-structural protein 3 in viral clearance in acute hepatitis C virus infection. Lancet, 1995. 346(8981): p. 1006-7]. The correlation of NS3-specific T cell responses to resolution of acute infection, in addition to its low genetic variably and relative large size makes the NS3 protein of HCV an attractive target for T-cell based DNA vaccines.

DNA vaccines have many conceptual advantages over more traditional vaccination methods, such as live attenuated viruses and recombinant protein-based vaccines. DNA vaccines are safe, stable, easily produced, and well tolerated in humans with preclinical trials indicating little evidence of plasmid integration [Martin, T., et al., Plasmid DNA malaria vaccine: the potential for genomic integration after intramuscular injection. Hum Gene Ther, 1.999. 10(5): p. 759-68; Nichols, W. W., et al., Potential DNA vaccine integration into host cell genome. Ann N Y Acad Sci, 1995. 772: p. 30-9]. In addition, DNA vaccines are well suited for repeated administration due to the fact that efficacy of the vaccine is not influenced by pre-existing antibody titers to the vector [Chattergoon, M., Boyer, and D. B. Weiner, Genetic immunization: a new era in vaccines and immune therapeutics. FASEB J, 1997. 11(10): p. 753-63]. However, one major obstacle for the clinical adoption of DNA vaccines has been a decrease in the platforms immunogenicity when moving to larger animals [Liu, M. A. and J. B. Ulmer, Human clinical trials of plasmid DNA vaccines. Adv Genet, 2005. 55: p. 25-40]. Recent technological advances in the engineering of DNA vaccine immunogen, such has codon optimization, RNA optimization and the addition of immunoglobulin leader sequences have improved expression and immunogenicity of DNA vaccines [Andre, S., et al., Increased immune response elicited by DNA vaccination with a synthetic gp120 sequence with optimized codon usage. J Virol, 1998. 72(2): p. 1497-503; Deml, L., et al., Multiple effects of codon usage optimization on expression and immunogenicity of DNA candidate vaccines encoding the human immunodeficiency virus type 1 Gag protein. J Virol, 2001. 75(22): p. 10991-1001; Laddy, D. J., et al., Immunogenicity of novel consensus-based DNA vaccines against avian influenza. Vaccine, 2007. 25(16): p. 2984-9; Frelin, L., et al., Codon optimization and mRNA amplification effectively enhances the immunogenicity of the hepatitis C virus nonstructural 3/4A gene. Gene Ther, 2004. 11(6): p. 522-33], as well as, recently developed technology in plasmid delivery systems such as electroporation [Hirao, L. A., et al., Intradermal/subcutaneous immunization by electroporation improves plasmid vaccine delivery and potency in pigs and rhesus macaques. Vaccine, 2008. 26(3): p. 440-8; Luckay, A., et al., Effect of plasmid DNA vaccine design and in vivo electroporation on the resulting vaccine-specific immune responses in rhesus macaques. J Virol, 2007. 81(10): p. 5257-69; Ahlen, G., et al., In vivo electroporation enhances the immunogenicity of hepatitis C virus nonstructural 3/4A DNA by increased local DNA uptake, protein expression, inflammation, and infiltration of CD3+ T cells. J Immunol, 2007. 179(7): p. 4741-53]. In addition, studies have suggested that the use of consensus immunogens may be able to increase the breadth of the cellular immune response as compared to native antigens alone [Yan., J., et al., Enhanced cellular immune responses elicited by an engineered HIV-1 subtype 13 consensus-based envelope DNA vaccine. Mol Ther, 2007. 15(2): p. 411-21; Rolland, M., et al., Reconstruction and function of ancestral center-of-tree human immunodeficiency virus type 1 proteins. J Virol, 2007. 81(16): p. 8507-14].

DNA vaccines encoding HCV NS3 and NS4 are disclosed in an article by Lang. K. A. et al, Vaccine (2008).

There remains a need for an effective vaccine against CV. There remains a need for effective methods of treating individuals infected with HCV.

SUMMARY OF THE INVENTION

Proteins comprising consensus HCV genotype 1a/1b NS3 and NS4A amino acid sequences and nucleic acid molecules that comprising a nucleotide sequence encoding such proteins are provided. These nucleic acid constructs and proteins encoded thereby provide improved immunogenic targets against which an anti-HCV immune response can be generated.

Constructs which encode such proteins sequences, vaccines which comprise such proteins and/or nucleic acid molecules that encode such proteins, and methods of inducing anti-HCV immune responses are also provided.

Nucleic acid molecules comprising a nucleotide sequence selected from the group consisting of: SEQ ID NO:1; fragments of SEQ ID NO:1; sequences having at least 90% homology to SEQ ID NO:1; and fragments of sequences having at least 90% homology to SEQ ID NO:1.

The present invention relates to nucleic acid molecules comprising a nucleotide sequence selected from the group consisting of: nucleotide sequences that encode SEQ ID NO:2; nucleotide sequences that encode an amino acid sequences having at least 90% homology to SEQ ID NO:2; fragments of nucleotide sequences that encode SEQ ID NO:2; fragments of a nucleotide sequence that encode an amino acid sequence having at least 90% homology to SEQ ID NO:2.

The present invention further provides pharmaceutical compositions comprising such nucleic acid molecules and their use in methods of inducing an immune response in an individual against HCV that comprise administering to an individual a composition comprising such nucleic acid molecules.

The present invention further provides recombinant vaccine comprising such nucleic acid molecules and their use in methods of inducing an immune response in an individual against HCV that comprise administering to an individual such a recombinant vaccine.

The present invention further provides live attenuated pathogens comprising such nucleic acid molecules and their use in methods of inducing an immune response in an individual against HCV that comprise administering to an individual such live attenuated pathogens.

Live Attenuated Pathogen

The present invention further provides proteins comprising amino acid sequences selected from the group consisting of: SEQ ID NO:2, sequences having at least 90% homology to SEQ ID NO:2; fragments of SEQ ID NO:2; and fragments of sequences having at least 90% homology to SEQ ID NO:2.

The present invention further provides pharmaceutical compositions comprising such proteins and their use in methods of inducing an immune response in an individual against HCV that comprise administering to an individual a composition comprising such proteins.

The present invention further provides recombinant vaccines comprising such proteins and their use in methods of inducing an immune response in an individual against HCV that comprise administering to an individual such a recombinant vaccine.

The present invention further provides live attenuated pathogens comprising such proteins and their use in methods of inducing an immune response in an individual against HCV that comprise administering to an individual such live attenuated pathogens.

DETAILED DESCRIPTION OF PREFERRED EMBODIMENTS

Figure 1:
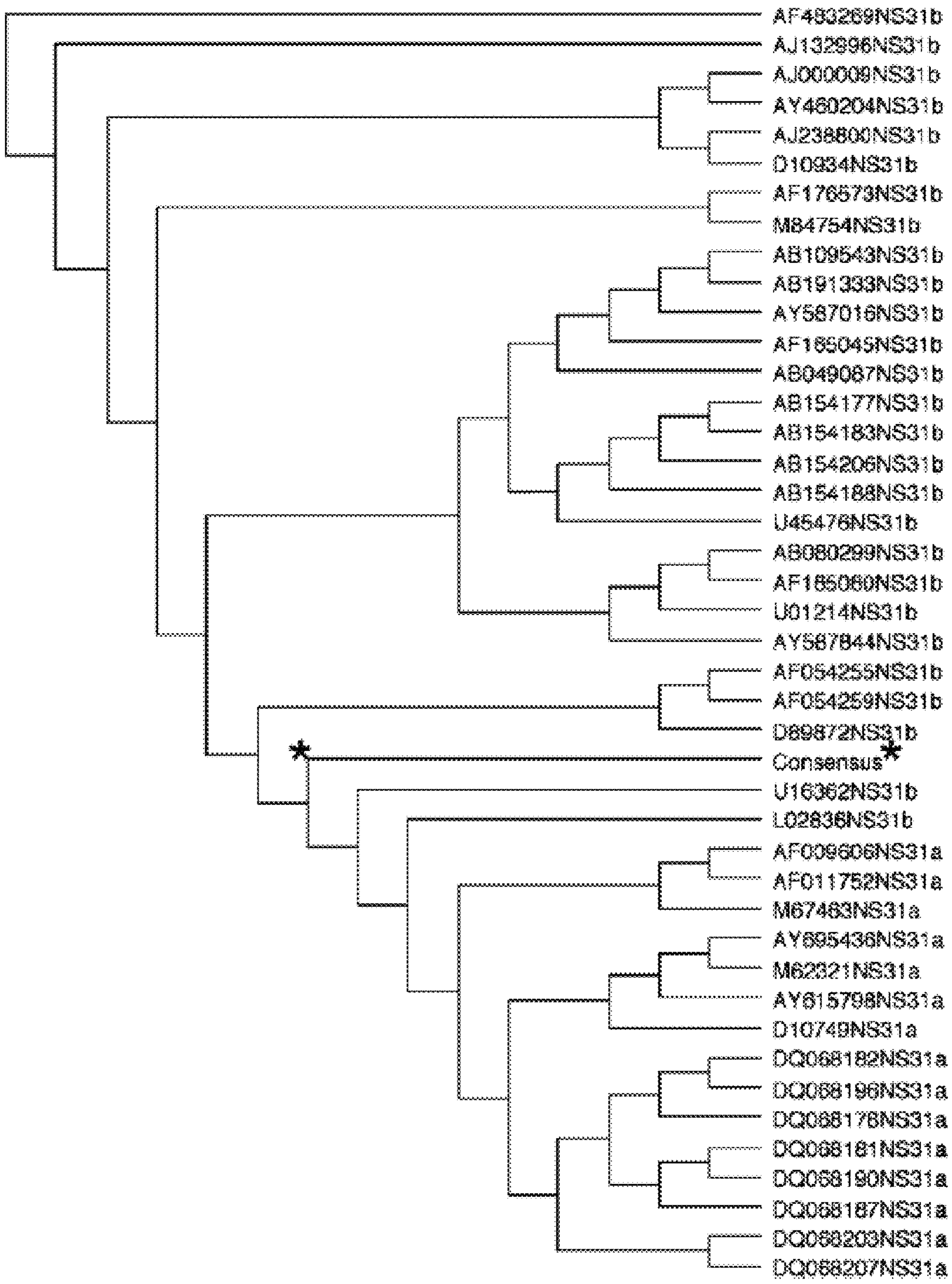
FIG. 1: Phylogenetic analysis of pConNS3/NS4A's genotype 1a/1b consensus sequence of NS3 as compared to individual genotype 1a and genotype 1b sequences for NS3. The genotype 1a/1b consensus sequence for NS3 was obtained from fifteen different HCV genotype 1a sequences and twenty-six different HCV genotype 1b sequences. The star represents the NS3 consensus sequence relative to its forty-one different component sequences.

As used herein, the phrase "stringent hybridization conditions" or "stringent conditions" refers to conditions under which a nucleic acid molecule will hybridize another a nucleic acid molecule, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present in excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g. 10 to 50 nucleotides) and at least about 60° C. for longer probes, primers or oligonucleotides. Stringent conditions may also be achieved with the addition of destabilizing agents, such as formamide.

Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP*4.0b10 software (D, L. Swofford, Sinauer Associates, Massachusetts). "Percentage of similarity" is calculated using PAUP*4.0b10 software (D. L. Swofford, Sinauer Associates, Massachusetts). The average similarity of the consensus sequence is calculated compared to all sequences in the phylogenic tree.

Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

As used herein, the term "genetic construct" refers to the DNA or RNA molecules that comprise a nucleotide sequence which encodes protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operable linked to a coding sequence that encodes a protein such that when present in the cell of the individual, the coding sequence will be expressed.

Improved vaccine are disclosed which arise from a multi-phase strategy to enhance cellular immune responses induced by immunogens. Modified consensus sequences were generated. Genetic modifications including codon optimization, RNA optimization, and the addition of a high efficient immunoglobin leader sequence are also disclosed. The novel construct has been designed to elicit stronger and broader cellular immune responses than a corresponding codon optimized immunogens.

The improved HCV vaccines are based upon proteins and genetic constructs that encode proteins with epitopes that make them particularly effective as immunogens against which anti-HCV can be induced. Accordingly, vaccines may induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of: one or more DNA vaccines, one or more recombinant vaccines, one or more protein subunit vaccines, one or more compositions comprising the immunogen, one or more attenuated vaccines and one or more killed vaccines.

According to some embodiments, a vaccine is delivered to an individual to modulate the activity of the individual's immune system and thereby enhance the immune response against HCV. When a nucleic acid molecules that encodes the protein is taken up by cells of the individual the nucleotide sequence is expressed in the cells and the protein are thereby delivered to the individual. Methods of delivering the coding sequences of the protein on nucleic acid molecule such as plasmid, as part of recombinant vaccines and as part of attenuated vaccines, as isolated proteins or proteins part of a vector are provided.

Compositions and methods are provided which prophylactically and/or therapeutically immunize an individual against HCV.

Compositions for delivering nucleic acid molecules that comprise a nucleotide sequence that encodes the immunogen are operably linked to regulatory elements. Compositions may include a plasmid that encodes the immunogen, a recombinant vaccine comprising a nucleotide sequence that encodes the immunogen, a live attenuated pathogen that encodes a protein of the invention and/or includes a protein of the invention; a killed pathogen includes a protein of the invention; or a composition such as a liposome or subunit vaccine that comprises a protein of the invention. The present invention further relates to injectable pharmaceutical compositions that comprise compositions.

SEQ ID NO:1 comprises a nucleotide sequence that encodes an HCV genotype 1a/1b consensus immunogen of HCV proteins NS3/NS4A. SEQ ID NO:1 further comprises an IgE leader sequence linked to the nucleotide sequence that encodes an HCV genotype 1a/1b consensus immunogen of HCV proteins NS3/NS4A. SEQ ID NO:2 comprises the amino acid sequence for the HCV genotype 1a/1b consensus immunogen of HCV proteins NS3/NS4A. SEQ ID NO:2 further comprises an IgE leader sequence linked to a consensus immunogen sequence. The IgE leader sequence is SEQ ID NO:4 and may be encoded by SEQ ID NO:3.

In some embodiments, vaccines of include SEQ ID NO:4, or a nucleic acid molecule that encodes SEQ ID NO:4. In some embodiments, vaccines preferably comprise SEQ ID NO:2 or a nucleic acid molecule that encodes it. In some embodiments, vaccines preferably comprise SEQ ID NO:1. Vaccines preferably include the IgE leader sequence SEQ ID NO:4 or nucleic acid sequence which encodes the same.

Fragments of SEQ ID NO:1 may comprise 90 or more nucleotides. In some embodiments, fragments of SEQ ID NO:1 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; in some embodiments, 1800 or more nucleotides; in some embodiments, 1890 or more nucleotides; in some embodiments, 1980 or more nucleotides; and in some embodiments, 2070 or more nucleotides. In some embodiments, fragments of SEQ ID NO:1 may comprise coding sequences for the IgE leader sequences. In some embodiments, fragments of SEQ ID NO:1 do not comprise coding sequences for the IgE leader sequences. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, and in some embodiments fewer than 675 nucleotides.

Fragments of SEQ ID NO:2 may comprise 30 or more amino acids. In some embodiments, fragments of SEQ ID NO:2 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids; in some embodiments, 510 or more amino acids; in some embodiments, 540 or more amino acids; in some embodiments, 570 or more amino acids; in some embodiments, 600 or more amino acids; in some embodiments, 630 or more amino acids; in some embodiments, 660 or more amino acid; and in some embodiments, 690 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, in some embodiments fewer than 450 amino acids, in some embodiments fewer than 480 amino acids, in some embodiments fewer than 540 amino acids, in some embodiments fewer than 600 amino acids, in some embodiments fewer than 660 amino acids, and in some embodiments fewer than 690 amino acids.

SEQ ID NO:5 comprises a nucleotide sequence that encodes an HCV genotype 1a/1b consensus immunogen of HCV proteins NS3/NS4A. SEQ ID NO:6 comprises the amino acid sequence for the HCV genotype 1a/1b consensus immunogen of HCV proteins NS3/NS4A.

Fragments of SEQ ID NO:5 may comprise 90 or more nucleotides. In some embodiments, fragments of SEQ ID NO:5 may comprise 180 or more nucleotides; in some embodiments, 270 or more nucleotides; in some embodiments 360 or more nucleotides; in some embodiments, 450 or more nucleotides; in some embodiments 540 or more nucleotides; in some embodiments, 630 or more nucleotides; in some embodiments, 720 or more nucleotides; in some embodiments, 810 or more nucleotides; in some embodiments, 900 or more nucleotides; in some embodiments, 990 or more nucleotides; in some embodiments, 1080 or more nucleotides; in some embodiments, 1170 or more nucleotides; in some embodiments, 1260 or more nucleotides; in some embodiments, 1350 or more nucleotides in some embodiments, 1440 or more nucleotides; in some embodiments, 1530 or more nucleotides; in some embodiments, 1620 or more nucleotides; in some embodiments, 1710 or more nucleotides; in some embodiments, 1800 or more nucleotides; in some embodiments, or more nucleotides. Fragments may comprise fewer than 180 nucleotides, in some embodiments fewer than 270 nucleotides, in some embodiments fewer than 360 nucleotides, in some embodiments fewer than 450 nucleotides, in some embodiments fewer than 540 nucleotides, in some embodiments fewer than 630 nucleotides, and in some embodiments fewer than 675 nucleotides.

Fragments of SEQ ID NO:6 may comprise 30 or more amino acids. In some embodiments, fragments of SEQ ID NO:6 may comprise 60 or more amino acids; in some embodiments, 90 or more amino acids; in some embodiments, 120 or more amino acids; in some embodiments; 150 or more amino acids; in some embodiments 180 or more amino acids; in some embodiments, 210 or more amino acids; in some embodiments, 240 or more amino acids; in some embodiments, 270 or more amino acids; in some embodiments, 300 or more amino acids; in some embodiments, 330 or more amino acids; in some embodiments, 360 or more amino acids; in some embodiments, 390 or more amino acids; in some embodiments, 420 or more amino acids; in some embodiments, 450 or more amino acids; in some embodiments, 480 or more amino acids. Fragments may comprise fewer than 90 amino acids, in some embodiments fewer than 120 amino acids, in some embodiments fewer than 150 amino acids, in some embodiments fewer than 180 amino acids, in some embodiments fewer than 210 amino acids, in some embodiments fewer than 240 amino acids, in some embodiments fewer than 270 amino acids, in some embodiments fewer than 300 amino acids, in some embodiments fewer than 330 amino acids, in some embodiments fewer than 360 amino acids, in some embodiments fewer than 390 amino acids, in some embodiments fewer than 420 amino acids, and in some embodiments fewer than 450 amino acids.

According to some embodiments, methods of inducing an immune response in individuals against an immunogen comprise administering to the individual the amino acid sequence for the HCV genotype 1a/1b consensus immunogen of HCV proteins NS3/NS4A, or functional fragments thereof, or expressible coding sequences thereof. Some embodiments comprise an isolated nucleic acid molecule that encodes the amino acid sequence for the HCV genotype 1a/1b consensus immunogen of HCV proteins NS3/NS4A or a fragment thereof. Some embodiments comprise a recombinant vaccine that encodes the amino acid sequence for the HCV genotype 1a/1b consensus immunogen of HCV proteins NS3/NS4A or a fragment thereof. Some embodiments comprise a subunit vaccine that comprises the amino acid sequence for the HCV genotype 1a/1b consensus immunogen of HCV proteins NS3/NS4A or a fragment thereof. Some embodiments comprise a live attenuated vaccine and/or a killed vaccine that comprise the amino acid sequence for the HCV genotype 1a/1b consensus immunogen of HCV proteins Improved vaccines comprise proteins and genetic constructs that encode proteins with epitopes that make them particularly effective as immunogens against which anti-HCV immune responses can be induced. Accordingly, vaccines can be provided to induce a therapeutic or prophylactic immune response. In some embodiments, the means to deliver the immunogen is a DNA vaccine, a recombinant vaccine, a protein subunit vaccine, a composition comprising the immunogen, an attenuated vaccine or a killed vaccine. In some embodiments, the vaccine comprises a combination selected from the groups consisting of one or more DNA vaccines, one or more recombinant vaccines, one or more protein subunit vaccines, one or more compositions comprising the immunogen, one or more attenuated vaccines and one or more killed vaccines.

According to some embodiments of the invention, a vaccine is delivered to an individual to modulate the activity of the individual's immune system and thereby enhance the immune response. When a nucleic acid molecules that encodes the protein is taken up by cells of the individual the nucleotide sequence is expressed in the cells and the protein are thereby delivered to the individual. Aspects of the invention provide methods of delivering the coding sequences of the protein on nucleic acid molecule such as plasmid, as part of recombinant vaccines and as part of attenuated vaccines, as isolated proteins or proteins part of a vector.

According to some aspects of the present invention, compositions and methods are provided which prophylactically and/or therapeutically immunize an individual DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036.006, which are both incorporated herein by reference.

The present invention relates to improved attenuated live vaccines, improved killed vaccines and improved vaccines that use recombinant vectors to deliver foreign genes that encode antigens and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

When taken up by a cell, the genetic construct(s) may remain present in the cell as a. functioning extrachromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV). Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode protein of the invention, and, additionally, genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1α, MIP-1p, IL-8, RANTES, L-selectin, P-selectin, E-selectin, CD34, GlyCAM-1, MadCAM-1, LFA-1, VLA-1, Mac-1, pl50.95, PECAM., ICAM-1, ICAM-2, ICAM-3, CD2, LFA-3, M-CSF, G-CSF, IL-4, mutant forms of IL-18, CD40, CD40L, vascular growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NRB, Bax, TRAIL, TRAIL-rec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA 1 or pcDNA3 (Invitrogen, San Diego, Calif.) may, for example, be used for production in mammalian cells such as Chinese Hamster Ovary cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination), recombinant vectors such as recombinant adenovirus, recombinant adenovirus associated virus and recombinant vaccinia.

Routes of administration include, but are not limited to, intramuscular, intranasally, intraperitoneal, intradermal, subcutaneous, intravenous, intraarterially, intraocularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, electroporation methods and devices, traditional syringes, needleless injection devices, or "microprojectile bombardment gone guns".

Examples of electroporation devices and electroporation methods preferred for facilitating delivery of the DNA vaccines, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007 all of which are hereby incorporated in their entirety.

The following is an example of an embodiment using electroporation technology, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The use of electroporation technology to deliver the improved HCV vaccine is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

In some embodiments, the nucleic acid molecule is delivered to the cells in conjunction with administration of a polynucleotide function enhancer or a genetic vaccine facilitator agent. Polynucleotide function enhancers are described in U.S. Pat. No. 5,593,972, U.S. Pat. No. 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The co-agents that are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF. In some embodiments, the nucleic acid molecule is provided in association with PLG to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses are provided. The vaccine may be a protein based, live attenuated vaccine, a cell vaccine, a recombinant vaccine or a nucleic acid or DNA vaccine. In some embodiments, methods of inducing an immune response in individuals against an immunogen, including methods of inducing mucosal immune responses, comprise administering to the individual one or more of CTACK protein, TECK protein, MEC protein and functional fragments thereof or expressible coding sequences thereof in combination with an isolated nucleic acid molecule that encodes protein of the invention and/or a recombinant vaccine that encodes protein of the invention and/or a subunit vaccine that protein of the invention and/or a live attenuated vaccine and/or a killed vaccine. The one or more of CTACK protein, TECK protein, MEC protein and functional fragments thereof may be administered prior to, simultaneously with or after administration of the isolated nucleic acid molecule that encodes an immunogen; and/or recombinant vaccine that encodes an immunogen and/or subunit vaccine that comprises an immunogen and/or live attenuated vaccine and/or killed vaccine. In some embodiments, an isolated nucleic acid molecule that encodes one or more proteins of selected from the group consisting of: CTACK, TECK, MEC and functional fragments thereof is administered to the individual.

The present invention is further illustrated in the following Example. It should be understood that this Example, while indicating embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Each of the U.S. patents, U.S. applications, and references cited throughout this disclosure are hereby incorporated in their entirety by reference.

EXAMPLE

Hepatitis C virus (HCV) represents a major health burden with more than 170 million individuals currently infected worldwide, equaling roughly 3% of the world's population. HCV preferentially infects hepatocytes and is able to persist in up to 70% of infected individuals. It is estimated that up to 30% of chronically infected individuals will go on to develop progressive liver disease as a result of HCV infection, making the virus the leading cause of liver transplantation in the world. Currently there is no vaccine for HCV. A multi-step approach was used to develop a novel genotype 1a/1b consensus HCV NS3/NS4A DNA vaccine able to induce strong cellular immunity. This construct is able to induce strong anti-NS3/NS4A T cell responses in C57BL/6 mice, as well as, in Rhesus Macaques.

Materials and Methods

Generation of HCV Genotype 1a/1b Consensus Sequence of NS3/NS4A

The consensus sequence for NS3 was generated from fifteen different genotype 1a sequences and twenty-six different genotype 1b sequences. The consensus sequence for NS4A was generated from fifteen different genotype 1a sequences and nineteen different genotype 1b sequences. The sequences were obtained from GenBank, chosen from multiple countries to avoid sampling error and aligned using Clustal X (version 1.8) software to generate the final NS3/NS4A consensus sequence.

Additional Modification of the NS3/NS4A Consensus Sequence

The consensus NS3/NS4A sequence was further modified through the addition of an IgE leader sequence, endoproteolytic cleavage site and a C-terminal HA tag, FIG. 1. GeneOptimizer™ (GENEART, Germany) was used to codon and RNA optimize the final sequence.

HCV NS3/NS4A DNA Immunogen

The final consensus NS3/NS4A fusion gene (ConNS3/NS4A) was synthesized and sequence verified by GENEART (Germany). ConNS3/NS4A was digested with BamH1 and Not1, and subcloned in to the clinical expression vector pVAX (Invitrogen) under the control of the CMV promoter. The final construct was named pConNS3/NS4A.

Immunofluorescence

Huh7.0 cells were transiently transfected with pConNS3/NS4A using Lipofectamine™ (Invitrogen) according to the manufacturer's guidelines. After 48 hours of transfection, the cells were permeabilized and expression of the proteins was determined using a mouse monoclonal antibody to the C-terminal HA tag of the fusion construct (Invitrogen) followed by a TRITC conjugated goat anti-mouse secondary antibody (Invitrogen).

Mouse Studies

Immunization/Electroporation

Female 6 to 8 week old C57BL/6 mice were purchased from Jackson Laboratories and were cared for in accordance with the National Institutes of Health and the University of Pennsylvania Institutional Care and Use Committee (IACUC) guidelines.

The mice were separated three mice per group and immunized with either pConNS3/NS4A or with the empty expression vector pVAX (negative control). Each mouse received three intramuscular injections, two weeks apart. Following each intramuscular injection, a three-electrode array made up of 26-gauge stainless steel electrodes was gently inserted into the muscle and a brief square-wave constant-current EKD was administered.

Splenocyte Isolation

The mice were sacrificed one week following the third immunization and the spleens were pooled according to group. The spleens were crushed using a Stomacher machine, and the resulting product was put through a 40 μM cell strainer to isolate the splenocytes. The cells were treated 5 min with ACK lysis buffer (Biosource) to clear the RBCs. Following lysis the splenocytes were resuspended in RPMI medium supplemented with 10% FBS. The cell number was determined with a hemocytometer.

IFN-Gamma ELISpot

The mouse IFN-gamma ELISpot assays were conducted as previously described [Yan., J., et al., Enhanced cellular immune responses elicited by an engineered HIV-1 subtype B consensus-based envelope DNA vaccine. Mol Ther, 2007. 15(2): p. 411-21]. Splenocytes were stimulated with five different pools of 15mer peptides, overlapping by 8 amino acids and spanning the entire length of the pConNS3/NS4A protein. The peptides were synthesized by Invitrogen and pooled at a concentration of 2 ug/ml/peptide. The splenocytes were plated at a concentration of 200,000 cells per well and the average number of spot forming units (SFU) was adjusted to $1\times10^6$ splenocytes for graphing purposes.

Epitope Mapping

The 15mer overlapping peptides were pooled into 21 separate pools, with each individual peptide represented in two pools of the 21 pools. Splenocytes were then stimulated with each pool in an IFN-gamma ELISpot assay as described above.

Rhesus Macaques Study

Study Design and Immunization

A total of five Rhesus Macaques of Indian origin were used and maintained in accordance with the Guide for the Care and Use of Laboratory Animals. Plasmids were prepared, HPLC purified (VGX Pharmaceuticals, Immune Therapeutics Division, The Woodlands, Tex.) and diluted in sterile water formulated with 1% (weight/weight) pol-L-glutamate sodium salt (MW=10.5 kDa) (Sigma).

The Macaques were intramuscularly injected followed by electroporation with the CELLECTRA™ adaptive constant current electroporation device and electrode arrays. Each monkey was injected with 1 mg of pConNS3/NS4A in 0.75 ml volume followed by three pulses of 0.5 Amp constant current, each 1 sec apart and 52 msec in length. Each monkey received two immunizations four weeks apart.

Blood Collection and PBMC Isolation

The Macaques were bled once before the first immunization and two weeks following each immunization. The animals were anesthetized with a mixture of ketamine (10 mg/kg) and acepromazine (0.1 mg/kg). Blood was collected in EDTA tubes and PBMCs were isolated using standard Ficoll-Hypaque density gradient centrifugation. The isolated PBMCs were resuspended complete media (RPMI 1640 with 2 mM/L L-glutamine supplemented with 10% heat inactivated FBS, 1× anti-biotic/anti-mycotic, and 55 μM/L β-mercaptoethanol).

IFN-gamma ELISpot assays were performed as previously described [Boyer, et al., SIV DNA vaccine co-administered with IL-12 expression plasmid enhances CD8 SIV cellular immune responses in cynomolgus macaques. J Med Primatol, 2005. 34(5-6): p. 262-70] using detection and capture antibodies from MabTech, Sweden.

Results

Construction of a Novel HCV Genotype 1a/1b Consensus Fusion Immunogen of HCV Structural Proteins NS3/NS4A Due to the high mutational rate of HCV, designing immunogens with multiple immune target sites is important not only for protection against various strains of the virus, but for maintaining control in chronically infected individuals by guarding against viral escape mutants. Previous findings report the use of consensus immunogens in the context of vaccines may be able to elicit a more broad immune response as compared to vaccination with the native immunogens alone. Based on these findings, a construct encoding the NS3/NS4A consensus sequence for HCV genotypes 1a/1b was designed in hopes of increasing the breadth of the immune response against the NS3/NS4A proteins. The consensus sequence was generated from a total of seventy-five different sequences obtained from GenBank. Clustal X (version 1.8) software was used to create multiple alignments needed to generate a single consensus sequence, FIG. 1.

Figure 2:
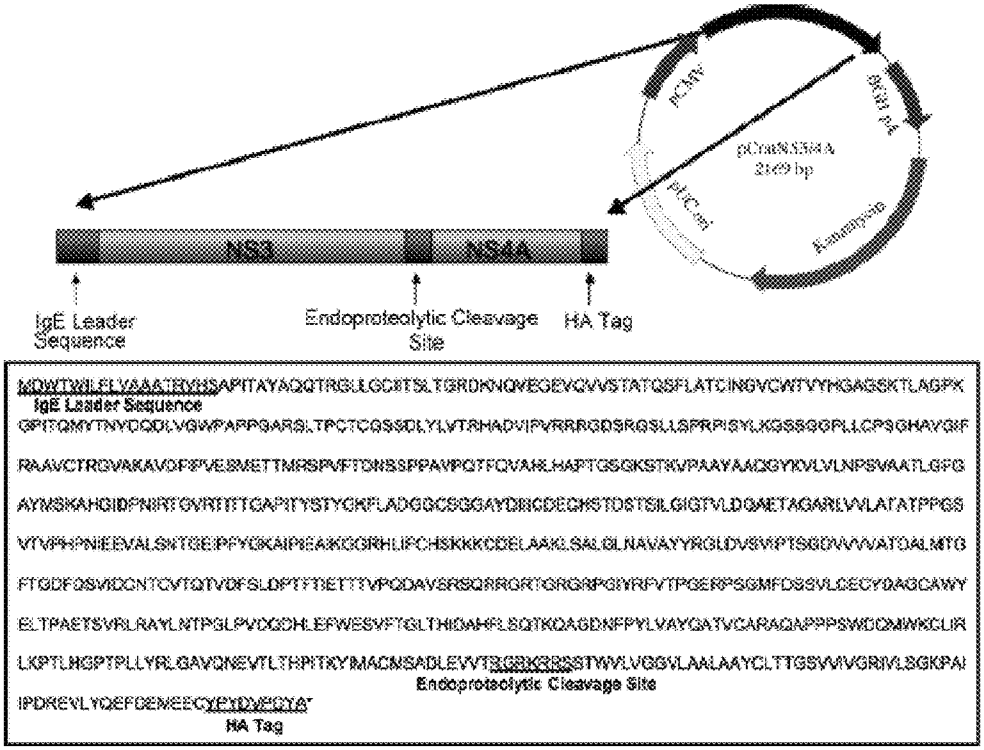
FIG. 2: Plasmid map and sequence of pConNS3/NS4A including SEQ ID NO:2. The sequences for the IgE leader, endoproteolytic cleavage site and C-terminal HA tag are underlined.

As depicted in FIG. 2, the consensus immunogen was further modified to increase expression and immunogenicity. NS4A was included within the construct due to its reported ability to enhance the stability, expression and immunogenicity of the NS3 protein [Frelin, L., et al., Low dose and gene gun immunization with a hepatitis C virus nonstructural (NS) 3 DNA-based vaccine containing NS4A inhibit NS3/4A-expressing tumors in vivo. Gene Ther, 2003. 10(8): p. 686-99; Wolk, B., et al., Subcellular localization, stability, and trans-cleavage competence of the hepatitis C virus NS3-NS4A complex expressed in tetracycline-regulated cell lines. J Virol, 2000. 74(5): p. 2293-304; Tanji, Y., et al., Hepatitis C virus-encoded nonstructural protein NS4A has versatile functions in viral protein processing. J Viral, 1995. 69(3): p. 1575-81]. An endoproteolytic cleavage site was introduced between the two protein sequences to ensure proper folding, as well as, better CTL processing. In addition, to further enhance expression of the construct, an IgE leader sequence was fused upstream of the start codon for the NS3 protein and the entire construct was codon and RNA optimized for expression in *Homo sapiens*. The final synthetically engineered ConNS3/NS4A gene was 2169 bp in length and was subcloned into the clinical expression vector pVAX using the BamH1 and Not1 restriction sites.

Expression of pConNS3/NS4A

Figure 3:
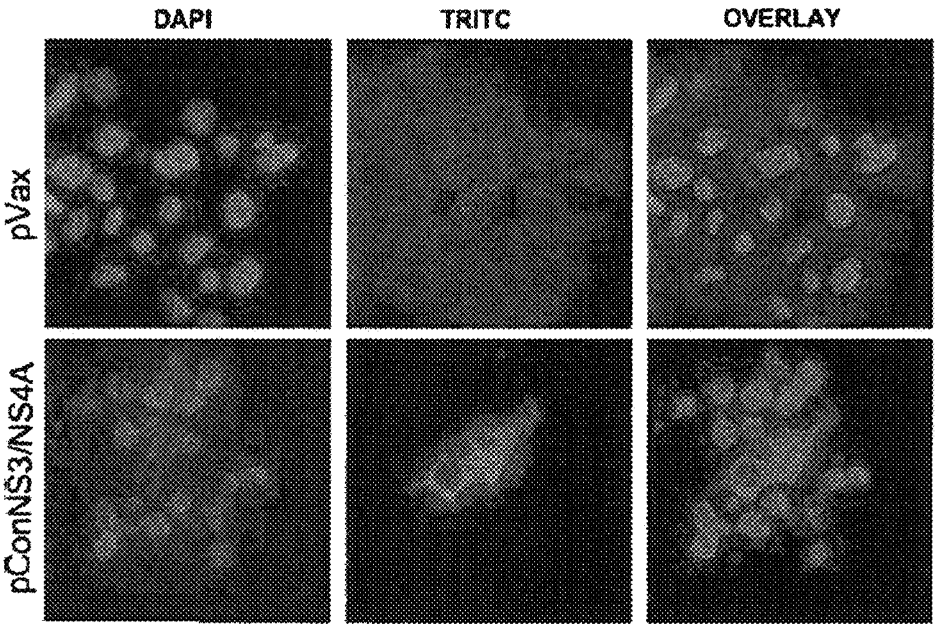
FIG. 3: Detection of pConNS3/NS4A expression via immunofluorescence (400×). Huh7.0 were transiently transfected with pConNS3/NS4A and expression of the gene product was detected using a monoclonal antibody against the C-terminal HA tag.

Expression of pConNS3/NS4A was confirmed through transient transfection of a Huh7.0 cell line with pConNS3/NS4A, FIG. 3. The translated proteins were detected with a monoclonal antibody against the C-terminal HA tag of the construct and were visualized using immunofluorescence. As a negative control, cells were also transiently transfected with the empty pVAX vector and stained with a monoclonal anti-HA antibody.

Figure 4:
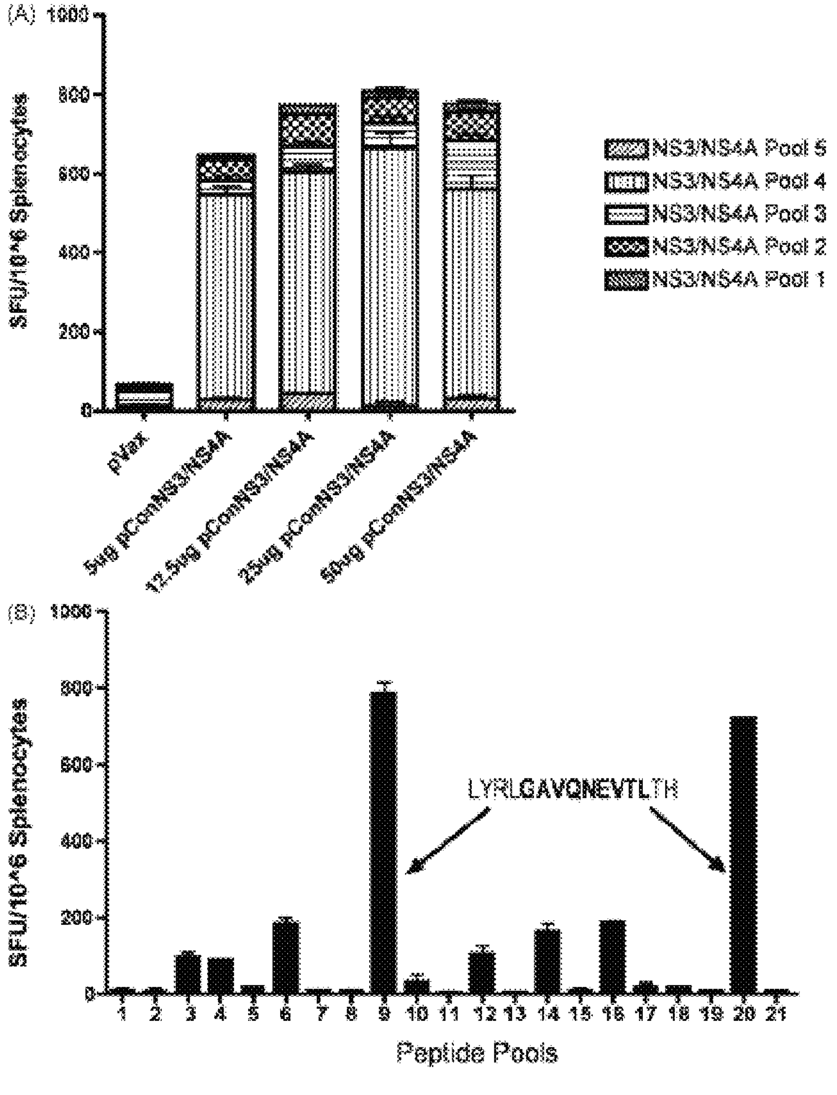
FIG. 4: pConNS3/NS4A induces strong NS3- and NS4-specific T cell responses in C57BL/6 mice. The number of NS3- and NS4-specific IFN-gamma spot forming units (SFU) per million splenocytes was determined through IFN-gamma ELISpot assays. (A) Five groups of mice, three mice per group, were immunized intramuscularly with either pVAX (negative control) or four different doses of pConNS3/NS4A: 5 ug, 12.5 ug, 25 ug or 50 ug followed by electroporation. Splenocytes were isolated from each mouse, pooled according to group and stimulated with five different pools of overlapping peptides spanning the entire length of the pConNS3/NS4A protein sequence. (B) Matrix epitope mapping of pConNS3/NS4A. Splenocytes were isolated from C57BL/6 mice immunized with 12.5 ug of pConNS3/NS4A and stimulated with 21 different pools of overlapping pConNS3/NS4A peptides with each peptide represented in two of the 21 pools. The dominant epitope was identified using IFN-gamma ELISpot assays as described above.

Immunization of C57BL/6 Mice with pConNS3/NS4A Induces Strong Cellular NS3- and NS4A-Specific Immune Responses Following confirmation of the expression of pConNS3/NS4A, mice were immunized intramuscularly with the construct, followed by electroporation, in order to determine whether pConNS3/NS4A could induce cellular immune responses in mice. C57BL/6 received three immunizations using four different doses of pConNS3/NS4A. The mice were sacrificed one week following the third immunization and cellular immune responses to the construct were determined using IFN-gamma ELI Spot assays. Splenocytes from vaccinated mice were stimulated with five pools of 15mer peptides overlapping by eight amino acids and spanning the sequence of pConNS3/NS4A. As shown in FIG. 4A, pConNS3/NS4A is able to induce potent cellular immune responses regardless of dose.

Next, using a matrix epitope mapping technique, the dominant epitope of pConNS3/NS4A was identified in IFN-gamma ELISpot assays. The dominant epitope of pConNS3/NS4A in C57BL/6 mice mapped to peptide 89 (LYRLGAVQNEVTLTH—SEQ ID NO:9) located near the C-terminus of the NS3 protein, FIG. 4B. This is supported by previous research which identified the nine amino acid sequence of GAVQNEVTH—SEQ ID NO:10, contained within peptide 89, as a dominant H-2b CTL epitope. This finding argues for normal and effective processing of our consensus immunogen.

Figure 5:
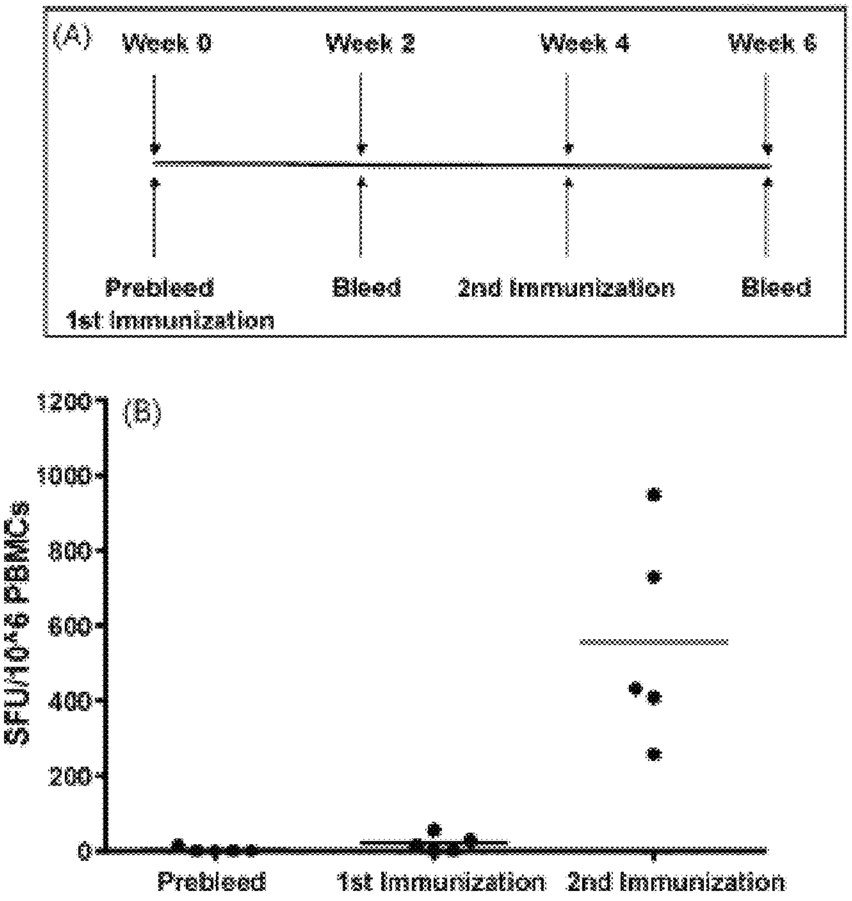
FIG. 5: pConNS3/NS4A induces strong NS3- and NS4-specific T cell responses in Rhesus Macaques. (A) Immunization schedule. Five Rhesus Macaques were immunized intramuscularly with 1 mg pConNS3/NS4A following by electroporation. The monkeys received two immunizations, four weeks apart. (B) Responses were measured once before the first immunization and two weeks following each immunization. The number of NS3- and NS4-specific IFN-gamma spot forming units (SFU) per million PBMCs was determined through IFN-gamma ELISpot assays.

Immunization of Rhesus Macaques with pConNS3/NS4A Induces Strong Cellular NS3- and NS4A-Specific Immune Responses Although immunogenic in small animal models, DNA vaccines have typically lost potency when moved into larger animals. However, encouraged by the strong cellular immune responses elicited by pConNS3/NS4A in mice, we decided to test the immunogenicity of the construct in a larger animal model. Rhesus Macaques were immunized IM/EP with pConNS3/NS4A two times, four weeks apart, FIG. 5A. The animals were bled once before the first immunization and two weeks following each immunization. The animals' immune responses to pConNS3/NS4A were determined with IFN-gamma ELISpot assays. FIG. 5B depicts the sum of each monkey's response to all five peptide pools, as well as, the average group response for each of the three time points. Cellular immune responses were not detectable following the prebleed and the first immunization, however, after the second immunization the responses increased dramatically to an average of 555+/−280 SFU/$10^6$ PBMCs. Therefore, following only two immunizations, pConNS3/NS4A was able to elicit clear NS3- and NS4-specific cellular immune responses.

pConNS3/NS4A Elicits a Broad Cellular Immune Response in Rhesus Macaques

Figure 6:
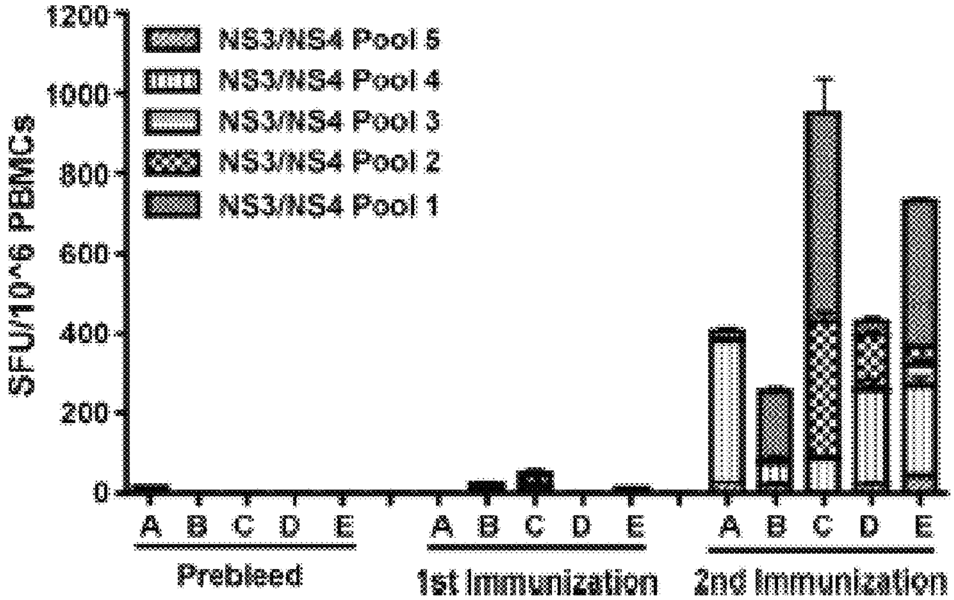
FIG. 6: pConNS3/NS4A induces broad cellular immune responses in Rhesus Macaques. Shown are the individual responses of the five monkeys to each of the five peptide pools, before immunization and two weeks following each immunization. The number of NS3- and NS4-specific IFN-gamma spot forming units (SFU) per million PBMCs was determined through IFN-gamma ELISpot assays.

Unlike immunization in C57BL/6 mice, where the majority of the immune response was directed at one dominant epitope of pConNS3/NS4A contained within a single peptide pool, the majority of immunized monkeys (4 out of 5) were able to elicit strong cellular immune responses to at least two or more peptide pools of pConNS3/NS4A, FIG. 6. Although further epitope mapping studies are planned, this suggests that the Rhesus Macaques were able to elicit cellular immune responses against multiple sites within the NS3/NS4A proteins. Therefore, the consensus sequence of pConNS3/NS4A is able to elicit both strong and broad cellular responses against the NS3/NS4A proteins in Rhesus Macaques.

Discussion

It is known that HCV infected individuals who recover from acute infection are able to mount early, multi-specific, CD4+ helper and CD8+ cytotoxic T-cell responses. It has also been reported that HCV-specific CTL responses are important for control of viral replication in chronically infected individuals [Rehermann, B., et al., Quantitative analysis of the peripheral blood cytotoxic T lymphocyte response in patients with chronic hepatitis C virus infection. J Clin Invest, 1996. 98(6): p. 1432-40; Nelson, D. R., et al., The role of hepatitis C virus-specific cytotoxic T lymphocytes in chronic hepatitis C. J Immunol, 1997. 158(3): p. 1473-81]. More specifically, a strong T cell response against the structural proteins of the virus, in particular the NS3 protein, has been reported to be an important correlate to clearance of acute infection. Due to the HCV virus's high mutation rate, the relatively conserved structural proteins of the virus, such as NS3, are attractive candidates for T cell based vaccines.

DNA vaccines are well suited for eliciting strong T cell responses. Unlike immunization with recombinant proteins, which tend to produce Th2 responses, DNA vaccines are able to induce strong Th1 responses due to the ability of antigens to be delivered and processed intracellularly. In addition, DNA vaccines theoretically have unlimited boosting capability and can be readministered as often as desired without fear of inducing neutralizing antibodies to the plasmid, as is the case with recombinant viral vectors.

Due to the importance of NS3 specific T cell responses in clearance of acute infection and control of chronic infection, as well as, the clear advantages of DNA immunization, a novel HCV DNA vaccine encoding the consensus sequence of genotype 1a and 1b for the HCV proteins NS3/NS4A (pConNS3/NS4A) was created. Although DNA vaccines are able to elicit strong cellular immune responses in small animals, the major obstacle for adoption of DNA vaccine into a clinical setting has been the reduced immunogenicity of the platform when introduced in larger animal models. Therefore, in order to improve the potency of our construct, a multi-step approach was taken in both its design and administration, including codon and RNA optimization, addition of an IgE leader sequence and administration of the construct with electroporation; modifications that have been shown to increase the expression and immunogenicity of DNA vaccines.

However, due to the high mutation rate of HCV, a construct able to elicit both strong and broad cellular immune responses targeting multiple sites within the immunogen may be better able to drive immunity against various strains of the virus, as well as, allow for better possible control of the virus in infected individuals by guarding against viral escape mutants. Previous studies report that incorporation of multiple sequences to create one consensus immunogen is able to produce broader immune responses. Therefore, as part of our construct design we incorporated seventy-five different HCV genotype 1a/1b sequences of the proteins NS3/NS4A in order to create one consensus immunogen.

The construct, pConNS3/NS4A, is expressed in cell culture, is able to induce strong NS3- and NS4-specific T cell responses in C57BL/6 mice following three immunizations, and is able to elicit both strong and broad NS3- and NS4A-specific T cell responses in a larger animal model, Rhesus Macaques, following only two immunizations. In fact, one of only two DNA vaccine studies looking at NS3-specific immune responses induced in Rhesus Macaques. While both studies used similar sequence optimization methods, plasmid delivery systems and identical vaccination schedules, this construct was able to induce much higher NS3 specific immune responses with fewer immunizations and one-fifth the amount of DNA as compared to a previous study in which animals received three immunizations of 5 mg of DNA [Capone, S., et al., Modulation of the immune response induced by gene electrotransfer of a hepatitis C virus DNA vaccine in nonhuman primates. J Immunol, 2006. 177(10): p. 7462-71]. In addition, pConNS3/NS4A is able to elicit broad responses in Rhesus Macaques. Unlike C57BL/6 mice, which responded to one dominant epitope contained within one peptide pool, the majority of the Rhesus Macaques were able to elicit strong cellular immune responses to multiple peptide pools, suggesting that these monkeys are able to mount a response to multiple epitopes within pConNS3/NS4A.

The invention claimed is:

1. A nucleic acid molecule comprising a nucleotide sequence selected from the group consisting of: SEQ ID NO:1; fragments of SEQ ID NO:1 comprising a nucleotide sequence of at least 1170 nucleotides of SEQ ID NO:1; and sequences having at least 90% homology to SEQ ID NO:1.

2. The nucleic acid molecule of claim 1 comprising SEQ ID NO:1.

3. The nucleic acid molecule of claim 1 comprising a sequence having at least 95% homology to SEQ ID NO:1.

4. The nucleic acid molecule of claim 1 comprising a sequence having at least 98% homology to SEQ ID NO:1.

5. The nucleic acid molecule of claim 1 comprising a sequence having at least 99% homology to a nucleotide sequence selected from the group consisting of: SEQ ID NO:1.

6. The nucleic acid molecule of claim 1 comprising SEQ ID NO:5.

7. The nucleic acid molecule of claim 1 comprising a nucleotide sequence that encodes SEQ ID NO:6.

8. The nucleic acid molecule of claim 1 wherein said molecule is a plasmid.

9. A pharmaceutical composition comprising a nucleic acid molecule of claim 8.

10. An injectable pharmaceutical composition comprising a nucleic acid molecule of claim 8.

11. A method of inducing an immune response in an individual against HCV comprising administering to said individual a composition comprising a nucleic acid molecule of claim 1.

12. The method of claim 11 wherein said nucleic acid molecule is a DNA molecule.

13. The method of claim 12 wherein said nucleic acid molecule is a plasmid.

14. The method of claim 12 wherein said nucleic acid molecule introduced into the individual by electroporation.

15. A recombinant vaccine comprising a nucleic acid molecule of claim 1.

16. The recombinant vaccine of claim 15 wherein said recombinant vaccine is a recombinant vaccinia vaccine.

17. A live attenuated vaccine comprising a nucleic acid molecule of claim 1.

18. A method of inducing an immune response in an individual against HCV comprising administering to said individual a recombinant vaccine of claim 15.

19. A method of inducing an immune response in an individual against HCV comprising administering to said individual a live attenuated vaccine of claim 17.

20. The method of claim 11 wherein the individual has been diagnosed as having HCV infection.

21. The nucleic acid molecule of claim 1 comprising a fragment of SEQ ID NO:1 comprising a nucleotide sequence of at least 1350 nucleotides of SEQ ID NO:1.

22. The nucleic acid molecule of claim 1 comprising a fragment of SEQ ID NO:1 comprising a nucleotide sequence of at least 1530 nucleotides of SEQ ID NO:1.

23. The nucleic acid molecule of claim 1 comprising a fragment of SEQ ID NO:1 comprising a nucleotide sequence of at least 1720 nucleotides of SEQ ID NO:1.

24. The nucleic acid molecule of claim 1 comprising a fragment of SEQ ID NO:1 comprising a nucleotide sequence of at least 1890 nucleotides of SEQ ID NO:1.

25. The nucleic acid molecule of claim 1 comprising a fragment of SEQ ID NO:1 comprising a nucleotide sequence of at least 2070 nucleotides of SEQ ID NO:1.

* * * * *

SEQUENCE LISTING

```
<160> NUMBER OF SEQ ID NOS: 10

<210> SEQ ID NO 1
<211> LENGTH: 2195
<212> TYPE: DNA
<213> ORGANISM: Artificial Sequence
<220> FEATURE:
<223> OTHER INFORMATION: synthetic HCV immunogen sequence comprising
      NS3/NS4A

<400> SEQUENCE: 1

ggtaccggat ccgccaccat ggactggacc tggattctgt tcctcgtggc tgctgctaca     60

agagtgcaca gcgcccccat caccgcctac gcccagcaga ccaggggcct gctgggctgc    120

atcatcacca gcctgaccgg cagggacaag aaccaggtgg agggcgaggt gcaggtggtg    180

tccaccgcca cccagagctt tctggccacc tgcatcaacg gcgtgtgctg gaccgtgtac    240

catggagccg gcagcaagac cctggccgga cccaagggcc ccatcaccca gatgtacacc    300

aacgtggatc aggatctggt cgggtggcct gcccctcctg gcgccagaag cctgaccccc    360

tgcacctgcg gcagcagcga cctgtacctg gtgacccggc acgccgacgt gatccccgtg    420

cggcggagag gcgattcccg gggcagcctg ctgtccccca ggcccatcag ctacctgaag    480

ggcagcagcg gcggacccct gctgtgccct agcggccacg ccgtgggcat cttcagagcc    540

gccgtgtgca ccaggggcgt ggccaaggcc gtggacttca tccccgtgga gagcatggaa    600

accaccatgc ggagccccgt gttcaccgac aacagcagcc ccccagctgt gccccagacc    660

ttccaggtgg cacatctgca cgcccctacc ggcagcggca agagcaccaa ggtgccagcc    720

gcctatgccg cccagggcta caaggtgctg gtgctgaacc cctccgtcgc tgctacactg    780

ggcttcggcg cctacatgag caaggcccac ggcatcgacc ccaacatccg gaccggcgtg    840

cggaccatca ccacaggcgc ccctatcaca tacagcacct acggcaagtt tctggccgac    900

ggcggctgta gcggcggagc ctacgacatc atcatctgcg acgagtgcca cagcaccgac    960

tccacctcca tcctgggcat cggcaccgtg ctggaccagg ccgagaccgc cggagccaga   1020

ctggtggtgc tggccaccgc cacacccccct ggcagcgtga ccgtgcccca ccccaatatc   1080

gaggaagtgg ccctgagcaa caccggcgag atccctttct acggcaaggc catccccatc   1140

gaggccatca agggcggcag gcacctgatc ttttgccaca gcaagaagaa gtgcgacgag   1200

ctggccgcca agctgtccgc cctgggcctg aacgccgtgg cctactaccg gggcctggac   1260

gtgagcgtga tccccacctc cggcgacgtg gtcgtggtcg ccacagacgc cctgatgacc   1320

ggcttcaccg gcgacttcga cagcgtgatc gactgcaaca cctgcgtgac ccagaccgtg   1380

gatttcagcc tggaccccac cttcaccatc gagaccacca ccgtgcctca ggacgccgtg   1440

agcagaagcc agcggagggg ccggaccggc agaggcaggc ccggcatcta ccggttcgtg   1500

acccctggcg agcggcccag cggcatgttc gacagcagcg tgctgtgcga gtgctacgac   1560
```

```
gccggctgcg cttggtatga gctgacccct gccgagacca gcgtgcggct gcgggcctac   1620

ctgaacaccc caggcctgcc cgtgtgccag gaccacctgg aattctggga gagcgtgttt   1680

accggcctga cccacatcga cgcccacttt ctgagccaga ccaagcaggc cggcgacaac   1740

ttcccctacc tggtggccta ccaggccacc gtgtgcgcca gagcccaggc ccctcccccc   1800

agctgggacc agatgtggaa gtgcctgatc cggctgaagc ccaccctgca cggcccaacc   1860

cccctgctgt accggctggg cgccgtgcag aacgaggtga ccctgaccca ccctatcacc   1920

aagtacatca tggcctgcat gagcgccgac ctggaagtgg tgaccagagg ccggaagcgg   1980

agaagcagca cctgggtgct cgtcggcgga gtgctggctg ctctcgccgc ctactgcctg   2040

accaccggca gcgtggtgat cgtgggccgg atcgtgctgt ccggcaagcc cgccatcatc   2100

cccgaccggg aggtgctgta ccaggaattc gacgaaatgg aagagtgcta cccctacgac   2160

gtgcccgact acgcctgatg agcggccgcg agtct                              2195
```

<210> SEQ ID NO 2
<211> LENGTH: 719
<212> TYPE: PRT
<213> ORGANISM: Artificial Sequence
<220> FEATURE:
<223> OTHER INFORMATION: synthetic HCV amino acid sequence comprising NS3/NS4A

<400> SEQUENCE: 2

```
Met Asp Trp Thr Trp Ile Leu Phe Leu Val Ala Ala Ala Thr Arg Val
1               5                   10                  15

His Ser Ala Pro Ile Thr Ala Tyr Ala Gln Gln Thr Arg Gly Leu Leu
            20                  25                  30

Gly Cys Ile Ile Thr Ser Leu Thr Gly Arg Asp Lys Asn Gln Val Glu
        35                  40                  45

Gly Glu Val Gln Val Val Ser Thr Ala Thr Gln Ser Phe Leu Ala Thr
    50                  55                  60

Cys Ile Asn Gly Val Cys Trp Thr Val Tyr His Gly Ala Gly Ser Lys
65                  70                  75                  80

Thr Leu Ala Gly Pro Lys Gly Pro Ile Thr Gln Met Tyr Thr Asn Val
                85                  90                  95

Asp Gln Asp Leu Val Gly Trp Pro Ala Pro Pro Gly Ala Arg Ser Leu
            100                 105                 110

Thr Pro Cys Thr Cys Gly Ser Ser Asp Leu Tyr Leu Val Thr Arg His
        115                 120                 125

Ala Asp Val Ile Pro Val Arg Arg Arg Gly Asp Ser Arg Gly Ser Leu
    130                 135                 140

Leu Ser Pro Arg Pro Ile Ser Tyr Leu Lys Gly Ser Ser Gly Gly Pro
145                 150                 155                 160

Leu Leu Cys Pro Ser Gly His Ala Val Gly Ile Phe Arg Ala Ala Val
                165                 170                 175

Cys Thr Arg Gly Val Ala Lys Ala Val Asp Phe Ile Pro Val Glu Ser
            180                 185                 190

Met Glu Thr Thr Met Arg Ser Pro Val Phe Thr Asp Asn Ser Ser Pro
        195                 200                 205

Pro Ala Val Pro Gln Thr Phe Gln Val Ala His Leu His Ala Pro Thr
    210                 215                 220

Gly Ser Gly Lys Ser Thr Lys Val Pro Ala Ala Tyr Ala Ala Gln Gly
225                 230                 235                 240
```

-continued

```
Tyr Lys Val Leu Val Leu Asn Pro Ser Val Ala Ala Thr Leu Gly Phe
                245                 250                 255

Gly Ala Tyr Met Ser Lys Ala His Gly Ile Asp Pro Asn Ile Arg Thr
            260                 265                 270

Gly Val Arg Thr Ile Thr Thr Gly Ala Pro Ile Thr Tyr Ser Thr Tyr
        275                 280                 285

Gly Lys Phe Leu Ala Asp Gly Gly Cys Ser Gly Gly Ala Tyr Asp Ile
    290                 295                 300

Ile Ile Cys Asp Glu Cys His Ser Thr Asp Ser Thr Ser Ile Leu Gly
305                 310                 315                 320

Ile Gly Thr Val Leu Asp Gln Ala Glu Thr Ala Gly Ala Arg Leu Val
                325                 330                 335

Val Leu Ala Thr Ala Thr Pro Pro Gly Ser Val Thr Val Pro His Pro
            340                 345                 350

Asn Ile Glu Glu Val Ala Leu Ser Asn Thr Gly Glu Ile Pro Phe Tyr
        355                 360                 365

Gly Lys Ala Ile Pro Ile Glu Ala Ile Lys Gly Gly Arg His Leu Ile
    370                 375                 380

Phe Cys His Ser Lys Lys Lys Cys Asp Glu Leu Ala Ala Lys Leu Ser
385                 390                 395                 400

Ala Leu Gly Leu Asn Ala Val Ala Tyr Tyr Arg Gly Leu Asp Val Ser
                405                 410                 415

Val Ile Pro Thr Ser Gly Asp Val Val Val Val Ala Thr Asp Ala Leu
            420                 425                 430

Met Thr Gly Phe Thr Gly Asp Phe Asp Ser Val Ile Asp Cys Asn Thr
        435                 440                 445

Cys Val Thr Gln Thr Val Asp Phe Ser Leu Asp Pro Thr Phe Thr Ile
    450                 455                 460

Glu Thr Thr Thr Val Pro Gln Asp Ala Val Ser Arg Ser Gln Arg Arg
465                 470                 475                 480

Gly Arg Thr Gly Arg Gly Arg Pro Gly Ile Tyr Arg Phe Val Thr Pro
                485                 490                 495

Gly Glu Arg Pro Ser Gly Met Phe Asp Ser Ser Val Leu Cys Glu Cys
            500                 505                 510

Tyr Asp Ala Gly Cys Ala Trp Tyr Glu Leu Thr Pro Ala Glu Thr Ser
        515                 520                 525

Val Arg Leu Arg Ala Tyr Leu Asn Thr Pro Gly Leu Pro Val Cys Gln
    530                 535                 540

Asp His Leu Glu Phe Trp Glu Ser Val Phe Thr Gly Leu Thr His Ile
545                 550                 555                 560

Asp Ala His Phe Leu Ser Gln Thr Lys Gln Ala Gly Asp Asn Phe Pro
                565                 570                 575

Tyr Leu Val Ala Tyr Gln Ala Thr Val Cys Ala Arg Ala Gln Ala Pro
            580                 585                 590

Pro Pro Ser Trp Asp Gln Met Trp Lys Cys Leu Ile Arg Leu Lys Pro
        595                 600                 605

Thr Leu His Gly Pro Thr Pro Leu Leu Tyr Arg Leu Gly Ala Val Gln
    610                 615                 620

Asn Glu Val Thr Leu Thr His Pro Ile Thr Lys Tyr Ile Met Ala Cys
625                 630                 635                 640

Met Ser Ala Asp Leu Glu Val Val Thr Arg Gly Arg Lys Arg Arg Ser
                645                 650                 655

Ser Thr Trp Val Leu Val Gly Gly Val Leu Ala Ala Leu Ala Ala Tyr
```

660 665 670

Cys Leu Thr Thr Gly Ser Val Val Ile Val Gly Arg Ile Val Leu Ser
675 680 685

Gly Lys Pro Ala Ile Ile Pro Asp Arg Glu Val Leu Tyr Gln Glu Phe
690 695 700

Asp Glu Met Glu Glu Cys Tyr Pro Tyr Asp Val Pro Asp Tyr Ala
705 710 715

<210> SEQ ID NO 3
<211> LENGTH: 72
<212> TYPE: DNA
<213> ORGANISM: Artificial Sequence
<220> FEATURE:
<223> OTHER INFORMATION: synthetic nucleic acid sequence encoding IgE leader

<400> SEQUENCE: 3
ggtaccggat ccgccaccat ggactggacc tggattctgt tcctcgtggc tgctgctaca 60
agagtgcaca gc 72

<210> SEQ ID NO 4
<211> LENGTH: 18
<212> TYPE: PRT
<213> ORGANISM: Artificial Sequence
<220> FEATURE:
<223> OTHER INFORMATION: synthetic IgE leader sequence

<400> SEQUENCE: 4

Met Asp Trp Thr Trp Ile Leu Phe Leu Val Ala Ala Ala Thr Arg Val
1 5 10 15

His Ser

<210> SEQ ID NO 5
<211> LENGTH: 2123
<212> TYPE: DNA
<213> ORGANISM: Artificial Sequence
<220> FEATURE:
<223> OTHER INFORMATION: synthetic HCV immunogen nucleotide sequence 2

<400> SEQUENCE: 5
gcccccatca ccgcctacgc ccagcagacc aggggcctgc tgggctgcat catcaccagc 60
ctgaccggca gggacaagaa ccaggtggag ggcgaggtgc aggtggtgtc caccgccacc 120
cagagctttc tggccacctg catcaacggc gtgtgctgga ccgtgtacca tggagccggc 180
agcaagaccc tggccggacc caagggcccc atcacccaga tgtacaccaa cgtggatcag 240
gatctggtcg ggtggcctgc ccctcctggc gccagaagcc tgacccccctg cacctgcggc 300 agcagcgacc tgtacctggt gacccggcac gccgacgtga tccccgtgcg gcggagaggc 360
gattcccggg gcagcctgct gtcccccagg cccatcagct acctgaaggg cagcagcggc 420
ggacccctgc tgtgccctag cggccacgcc gtgggcatct tcagagccgc cgtgtgcacc 480
aggggcgtgg ccaaggccgt ggacttcatc cccgtggaga gcatggaaac caccatgcgg 540
agccccgtgt tcaccgacaa cagcagcccc ccagctgtgc cccagacctt ccaggtggca 600
catctgcacg cccctaccgg cagcggcaag agcaccaagg tgccagccgc ctatgccgcc 660
cagggctaca aggtgctggt gctgaacccc tccgtcgctg ctacactggg cttcggcgcc 720
tacatgagca aggcccacgg catcgacccc aacatccgga ccggcgtgcg gaccatcacc 780
acaggcgccc ctatcacata cagcacctac ggcaagtttc tggccgacgg cggctgtagc 840

```
ggcggagcct acgacatcat catctgcgac gagtgccaca gcaccgactc cacctccatc    900

ctgggcatcg gcaccgtgct ggaccaggcc gagaccgccg gagccagact ggtggtgctg    960

gccaccgcca cacccctgg cagcgtgacc gtgccccacc ccaatatcga ggaagtggcc    1020

ctgagcaaca ccggcgagat ccctttctac ggcaaggcca tccccatcga ggccatcaag   1080

ggcggcaggc acctgatctt ttgccacagc aagaagaagt gcgacgagct ggccgccaag   1140

ctgtccgccc tgggcctgaa cgccgtggcc tactaccggg gcctggacgt gagcgtgatc   1200

cccacctccg gcgacgtggt cgtggtcgcc acagacgccc tgatgaccgg cttcaccggc   1260

gacttcgaca gcgtgatcga ctgcaacacc tgcgtgaccc agaccgtgga tttcagcctg   1320

gaccccacct tcaccatcga gaccaccacc gtgcctcagg acgccgtgag cagaagccag   1380

cggaggggcc ggaccggcag aggcaggccc ggcatctacc ggttcgtgac ccctggcgag   1440

cggcccagcg gcatgttcga cagcagcgtg ctgtgcgagt gctacgacgc cggctgcgct   1500

tggtatgagc tgacccctgc cgagaccagc gtgcggctgc gggcctacct gaacacccca   1560

ggcctgcccg tgtgccagga ccacctggaa ttctgggaga gcgtgtttac cggcctgacc   1620

cacatcgacg cccactttct gagccagacc aagcaggccg gcgacaactt cccctacctg   1680

gtggcctacc aggccaccgt gtgcgccaga gcccaggccc ctccccccag ctgggaccag   1740

atgtggaagt gcctgatccg gctgaagccc accctgcacg gcccaacccc cctgctgtac   1800

cggctgggcg ccgtgcagaa cgaggtgacc ctgacccacc ctatcaccaa gtacatcatg   1860

gcctgcatga gcgccgacct ggaagtggtg accagaggcc ggaagcggag aagcagcacc   1920

tgggtgctcg tcggcggagt gctggctgct ctcgccgcct actgcctgac caccggcagc   1980

gtggtgatcg tgggccggat cgtgctgtcc ggcaagcccg ccatcatccc cgaccgggag   2040

gtgctgtacc aggaattcga cgaaatggaa gagtgctacc cctacgacgt gcccgactac   2100

gcctgatgag cggccgcgag tct                                           2123
```

```
<210> SEQ ID NO 6
<211> LENGTH: 692
<212> TYPE: PRT
<213> ORGANISM: Artificial Sequence
<220> FEATURE:
<223> OTHER INFORMATION: synthetic HCV immunogen amino acid sequence 2

<400> SEQUENCE: 6

Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Val Val Ser Thr Ala Thr Gln Ser Phe Leu Ala Thr Cys Ile
        35                  40                  45

Asn Gly Val Cys Trp Thr Val Tyr His Gly Ala Gly Ser Lys Thr Leu
    50                  55                  60

Ala Gly Pro Lys Gly Pro Ile Thr Gln Met Tyr Thr Asn Val Asp Gln
65                  70                  75                  80

Asp Leu Val Gly Trp Pro Ala Pro Pro Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
```

-continued

```
    130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Ile Pro Val Glu Ser Met Glu
                165                 170                 175

Thr Thr Met Arg Ser Pro Val Phe Thr Asp Asn Ser Ser Pro Pro Ala
            180                 185                 190

Val Pro Gln Thr Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ala Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ser Thr Ser Ile Leu Gly Ile Gly
    290                 295                 300

Thr Val Leu Asp Gln Ala Glu Thr Ala Gly Ala Arg Leu Val Val Leu
305                 310                 315                 320

Ala Thr Ala Thr Pro Pro Gly Ser Val Thr Val Pro His Pro Asn Ile
                325                 330                 335

Glu Glu Val Ala Leu Ser Asn Thr Gly Glu Ile Pro Phe Tyr Gly Lys
            340                 345                 350

Ala Ile Pro Ile Glu Ala Ile Lys Gly Gly Arg His Leu Ile Phe Cys
        355                 360                 365

His Ser Lys Lys Lys Cys Asp Glu Leu Ala Ala Lys Leu Ser Ala Leu
    370                 375                 380

Gly Leu Asn Ala Val Ala Tyr Tyr Arg Gly Leu Asp Val Ser Val Ile
385                 390                 395                 400

Pro Thr Ser Gly Asp Val Val Val Val Ala Thr Asp Ala Leu Met Thr
                405                 410                 415

Gly Phe Thr Gly Asp Phe Asp Ser Val Ile Asp Cys Asn Thr Cys Val
            420                 425                 430

Thr Gln Thr Val Asp Phe Ser Leu Asp Pro Thr Phe Thr Ile Glu Thr
        435                 440                 445

Thr Thr Val Pro Gln Asp Ala Val Ser Arg Ser Gln Arg Arg Gly Arg
    450                 455                 460

Thr Gly Arg Gly Arg Pro Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Ser Val Arg
            500                 505                 510

Leu Arg Ala Tyr Leu Asn Thr Pro Gly Leu Pro Val Cys Gln Asp His
        515                 520                 525

Leu Glu Phe Trp Glu Ser Val Phe Thr Gly Leu Thr His Ile Asp Ala
    530                 535                 540

His Phe Leu Ser Gln Thr Lys Gln Ala Gly Asp Asn Phe Pro Tyr Leu
545                 550                 555                 560
```

Val Ala Tyr Gln Ala Thr Val Cys Ala Arg Ala Gln Ala Pro Pro Pro
            565                 570                 575

Ser Trp Asp Gln Met Trp Lys Cys Leu Ile Arg Leu Lys Pro Thr Leu
        580                 585                 590

His Gly Pro Thr Pro Leu Leu Tyr Arg Leu Gly Ala Val Gln Asn Glu
    595                 600                 605

Val Thr Leu Thr His Pro Ile Thr Lys Tyr Ile Met Ala Cys Met Ser
610                 615                 620

Ala Asp Leu Glu Val Val Thr Arg Gly Arg Lys Arg Arg Ser Ser Thr
625                 630                 635                 640

Trp Val Leu Val Gly Gly Val Leu Ala Ala Leu Ala Ala Tyr Cys Leu
            645                 650                 655

Thr Thr Gly Ser Val Val Ile Val Gly Arg Ile Val Leu Ser Gly Lys
            660                 665                 670

Pro Ala Ile Ile Pro Asp Arg Glu Val Leu Tyr Gln Glu Phe Asp Glu
        675                 680                 685

Met Glu Glu Cys
    690

<210> SEQ ID NO 7
<211> LENGTH: 30
<212> TYPE: DNA
<213> ORGANISM: Artificial Sequence
<220> FEATURE:
<223> OTHER INFORMATION: synthetic nucleic acid sequence of antigen
      component 1

<400> SEQUENCE: 7
tacccctacg acgtgcccga ctacgcctga                                      30

<210> SEQ ID NO 8
<211> LENGTH: 9
<212> TYPE: PRT
<213> ORGANISM: Artificial Sequence
<220> FEATURE:
<223> OTHER INFORMATION: synthetic amino acid sequence of antigen
      component 1

<400> SEQUENCE: 8

Tyr Pro Tyr Asp Val Pro Asp Tyr Ala
1               5

<210> SEQ ID NO 9
<211> LENGTH: 15
<212> TYPE: PRT
<213> ORGANISM: Artificial Sequence
<220> FEATURE:
<223> OTHER INFORMATION: peptide 89

<400> SEQUENCE: 9

Leu Tyr Arg Leu Gly Ala Val Gln Asn Glu Val Thr Leu Thr His
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: dominant H-2b CTL epitope of peptide 89

-continued

<400> SEQUENCE: 10

Gly Ala Val Gln Asn Glu Val Thr His
1 5